United States Patent
Barkley et al.

(10) Patent No.: US 6,173,203 B1
(45) Date of Patent: Jan. 9, 2001

(54) CIRCUIT MOUNTING SYSTEM FOR AUTOMATED EXTERNAL DEFIBRILLATOR CIRCUITS

(75) Inventors: Steven D. Barkley, Champlin; Robert K. Johnson, Blaine, both of MN (US)

(73) Assignee: SurVivaLink Corpration, Minneapolis, MN (US)

( * ) Notice: Under 35 U.S.C. 154(b), the term of this patent shall be extended for 0 days.

(21) Appl. No.: 09/056,940

(22) Filed: Apr. 8, 1998

Related U.S. Application Data

(60) Provisional application No. 60/041,808, filed on Apr. 8, 1997.

(51) Int. Cl.⁷ ............................................. A61N 1/39
(52) U.S. Cl. ................................. 607/5; 607/36
(58) Field of Search ................... 607/36, 5, 2, 4

(56) References Cited

U.S. PATENT DOCUMENTS

| | | | |
|---|---|---|---|
| 3,842,842 | * 10/1974 | Kenny et al. | 607/36 |
| 4,254,775 | * 3/1981 | Langer | 607/5 |
| 5,645,586 | * 7/1997 | Meltzer | 623/11 |
| 5,691,881 | * 11/1997 | McDonough | 361/682 |
| 5,741,313 | * 4/1998 | Davis et al. | 607/36 |
| 5,749,910 | * 5/1998 | Brumwell et al. | 607/36 |
| 5,802,188 | * 9/1998 | McDonough | 381/159 |
| 5,814,090 | * 9/1998 | Latterell et al. | 607/36 |
| 5,843,131 | * 12/1998 | McDonough | 607/5 |
| 5,873,899 | * 2/1999 | Stutz, Jr. et al. | 607/36 |
| 5,895,980 | * 4/1999 | Thompson | 607/36 |

* cited by examiner

Primary Examiner—Kennedy Schaetzle
(74) Attorney, Agent, or Firm—Patterson, Thuente, Skaar & Christensen, P.A.

(57) ABSTRACT

A floating mounting structure is provided for protectively mounting an electronic circuitry system within an automated external defibrillator case. A method of assembling an electronic circuitry system within an automated external defibrillator case is also provided. A circuit mounting system is utilized and includes a spacer and a shock mount. The spacer may include cut out portions to accommodate raised elements on circuit boards of the electronic circuitry system. The spacer is disposed between two circuit boards which may be affixed to each other. The affixed circuit boards and spacer are folded within the shock mount and disposed within the defibrillator case. Alternatively, a single mounting structure may be used to secure and protect the circuit board within the defibrillator case. A shielding may be present on an exterior surface of the foam mounting structures to protect the electronic circuitry from electromagnetic interference.

7 Claims, 9 Drawing Sheets

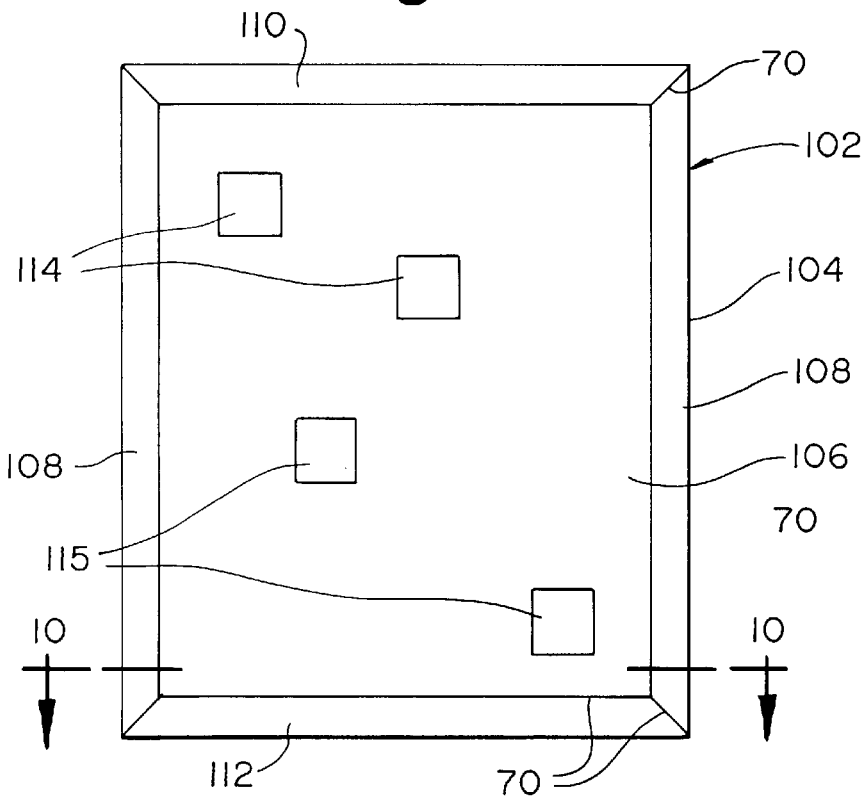
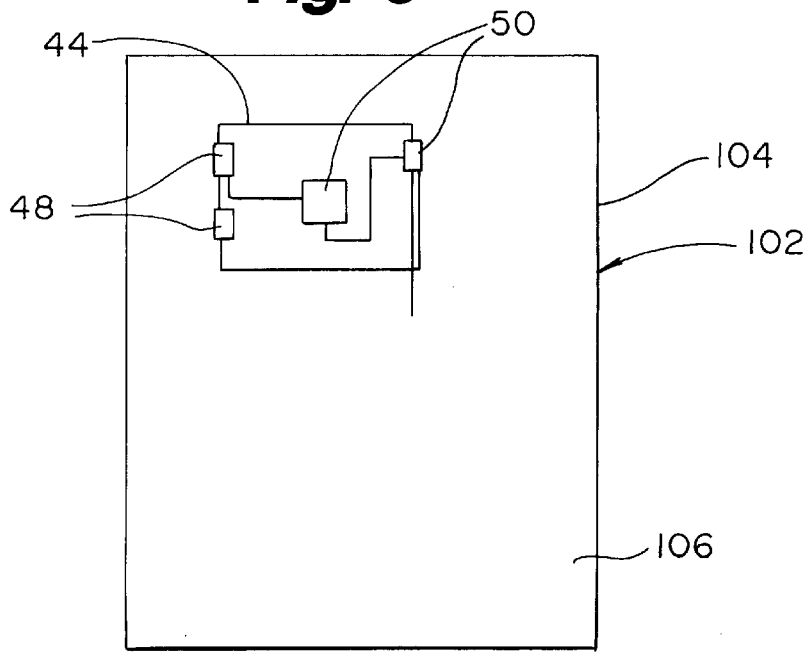

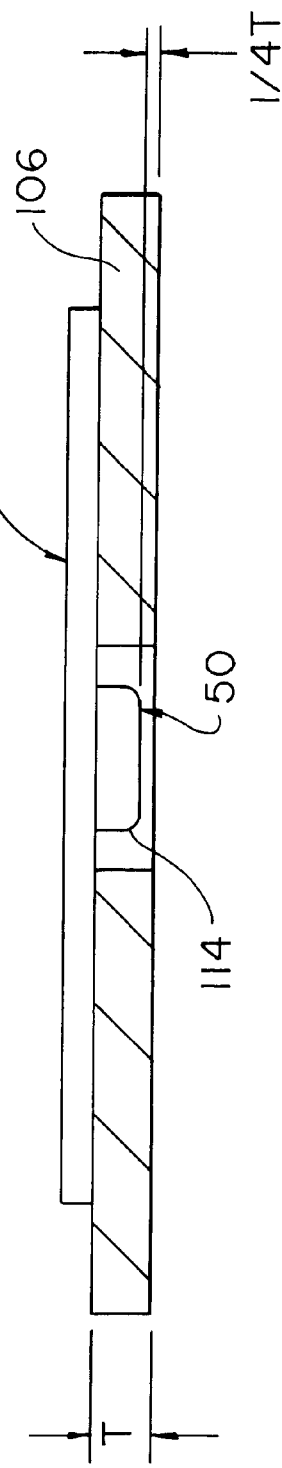
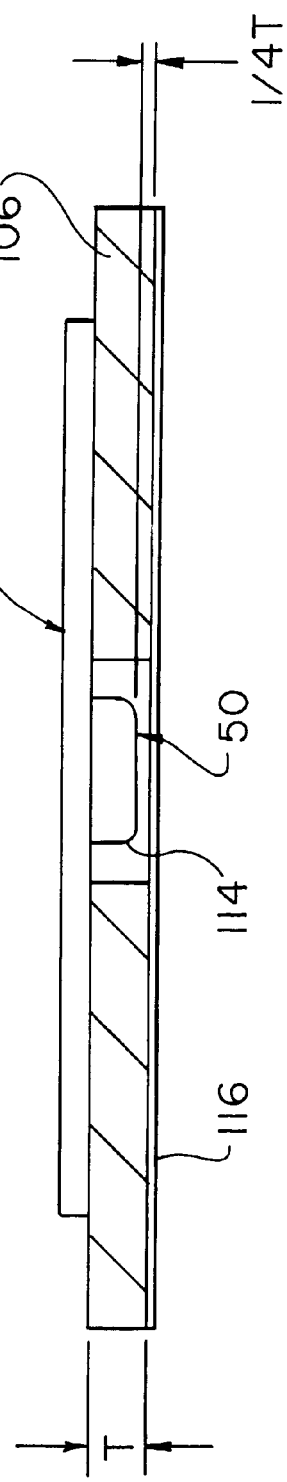

CIRCUIT MOUNTING SYSTEM FOR AUTOMATED EXTERNAL DEFIBRILLATOR CIRCUITS

CROSS-REFERENCES TO RELATED INVENTIONS

This application is related to and claims the benefit of U.S. Provisional Application Ser. No. 60/041,808, filed Apr. 8, 1997, the contents of which are incorporated herein by reference.

FIELD OF THE INVENTION

The present invention relates to automated external defibrillator circuit boards. In particular, the present invention relates to a cushioned material for mounting and protecting automated external defibrillator circuit boards within an automated external defibrillator housing and for providing conductive shielding from electromagnetic interference.

BACKGROUND OF THE INVENTION

Automated external defibrillators (AEDs) are often used by such emergency response personnel as police and paramedics. Consequently, AEDs are often stored in automobiles and ambulances in places where they are often jolted during transport. Moreover, in responding to emergencies, AEDs must often be quickly carried from vehicles to the site of a patient in extreme need of defibrillation. In being carried and utilized, AEDs may be dropped or knocked off raised horizontal surfaces. However, in order to function properly, the inner circuitry of AEDs must not sustain damage. Thus, there is a need to provide AEDs with the ability to sustain the jarring, dropping and other abuse inherent in an emergency situation.

One method of mounting circuit boards in AEDs is with screws. In this manner, the circuit boards are fixedly screwed to mounting posts inside the AED housing. However, when screws are utilized to fix circuit boards, assembly time, hence manufacturing cost, is increased. Moreover, during drop tests with circuit boards fixedly screwed into an AED housing, impact forces may approach 100–500 Gs when the AED strikes the floor. When screws are utilized to affix circuit boards to AED housings, the circuit boards are not cushioned against damages resulting from these forces.

Exposure of a defibrillator circuit board to electromagnetic interference during recharge, testing and defibrillation can result in malfunction, misdiagnosis of the readiness state of the device for defibrillation and a failure of the device to function during recharge or defibrillation. One alternative is to manufacture the AED housing with a metallic lining. However, this practice adds to the expense of the product.

It would be desirable to provide a cushioned mounting which protects circuit boards from damage, provides an efficient and low cost method of affixing circuit boards to AED housing during manufacture, and which provides for shielding from electromagnetic interference.

SUMMARY OF THE INVENTION

The present invention is an automated external defibrillator circuit (AED) mounting structure wherein at least one circuit board is mounted in an AED housing. A die cut foam mounting structure according to the present invention is provided for mounting the at least one circuit board in the housing. The die cut foam mounting structure according to the present invention has a plurality of receiving cavities formed therein to receive various circuit components from the circuit board. The die cut foam of the present invention is preferably a closed cell low cell density polyurethane. In an alternative embodiment of the present invention, the foam further includes a metal foil bonded to the foam which provides conductive shielding from electromagnetic interference. This provides a cost savings by allowing the elimination of the shielding currently used in an AED.

The present invention also provides a method for assembling an electronic circuitry system within an AED case. The defibrillator case of the preferred embodiment includes a case lower portion and a case upper portion. The electronic circuitry system includes a first and second circuit board, each circuit board with a raised element, a first die cut foam mounting structure with a first and second cut out portion, and a second die cut foam mounting structure. The preferred method includes disposing the first circuit board proximate the first mounting structure such that the raised element is accommodated by the first cut out portion. The first mounting structure and the first circuit board are then placed within the case lower portion. The case upper portion and the case lower portion are then mated and secured together.

BRIEF DESCRIPTION OF THE DRAWINGS

FIG. 8 is a top plan view of an alternate embodiment of a circuit board mounting structure.

FIG. 9 is a top plan view in which a circuit board is disposed on the alternate embodiment of FIG. 8.

FIG. 10 is a cross-sectional view of a circuit board positioned on the alternate embodiment of FIG. 8, taken along line 10—10 of FIG. 8.

FIG. 11 is a cross-sectional view of an alternate embodiment to that shown in FIGS. 8, 9 and 10.

DETAILED DESCRIPTION

The present invention is a circuit mounting structure for automated external defibrillators (AEDs). In order to facilitate a full appreciation of the invention, an overview of the preferred embodiment is initially provided. The overview is followed by a more detailed explanation.

As previously stated, the present invention is a circuit mounting structure for AEDs. AEDs are used for emergency treatment of victims of cardiac arrest and are typically used by first responders. AEDs automatically analyze a patient's cardiac electrical signals and advise the user to apply a defibrillation shock if ventricular fibrillation, ventricular tachycardia or other cardiac rhythms with ventricular rates exceeding 180 beats per minute and having amplitudes of at least 0.15 millivolts are detected. When such a condition is detected, the device will build up an electrical charge. Then it will notify the user with an audible charge tone, a voice prompt and a flashing red rescue button that a defibrillation shock can be administered. Finally, the AED will deliver the defibrillation shock through electrodes when the flashing red rescue button is pressed.

Figure 1:
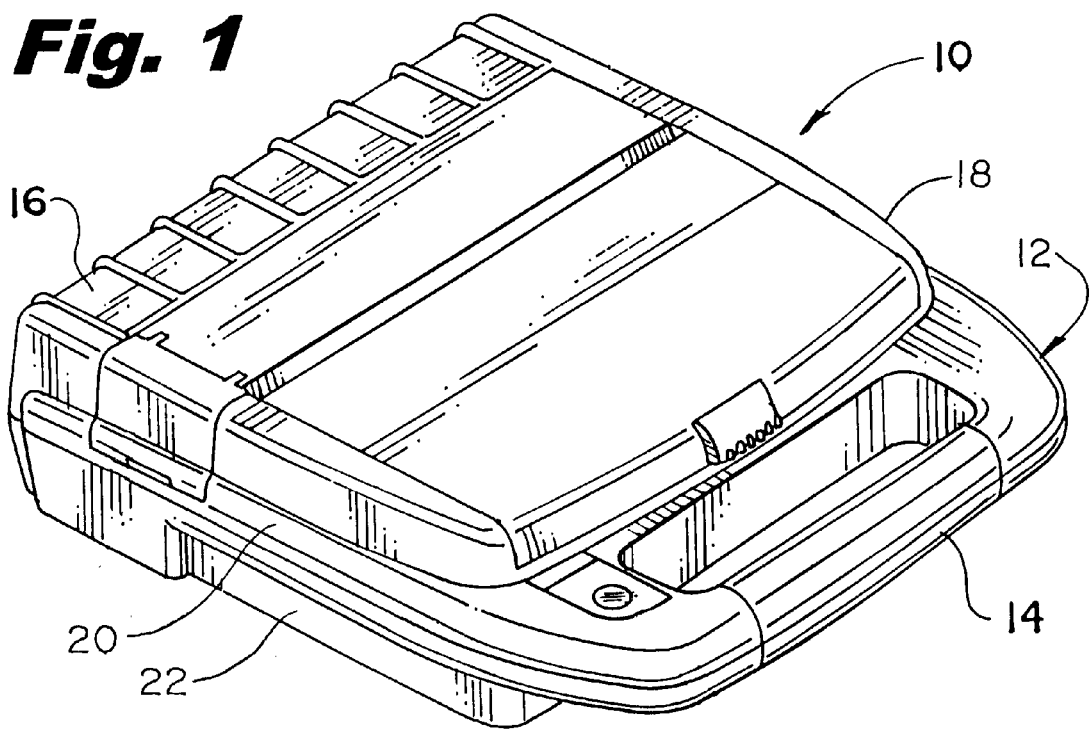
FIG. 1 is a perspective view of an AED.

An AED 10 is illustrated generally in FIG. 1. An exemplary embodiment of AED 10 is described in U.S. Pat. No. 5,645,571, assigned to the assignee of the present invention, the disclosure of which is hereby incorporated by reference. This AED embodiment is commercially available from SurVivaLink Corporation of Minnetonka, Minn.

Figure 2:
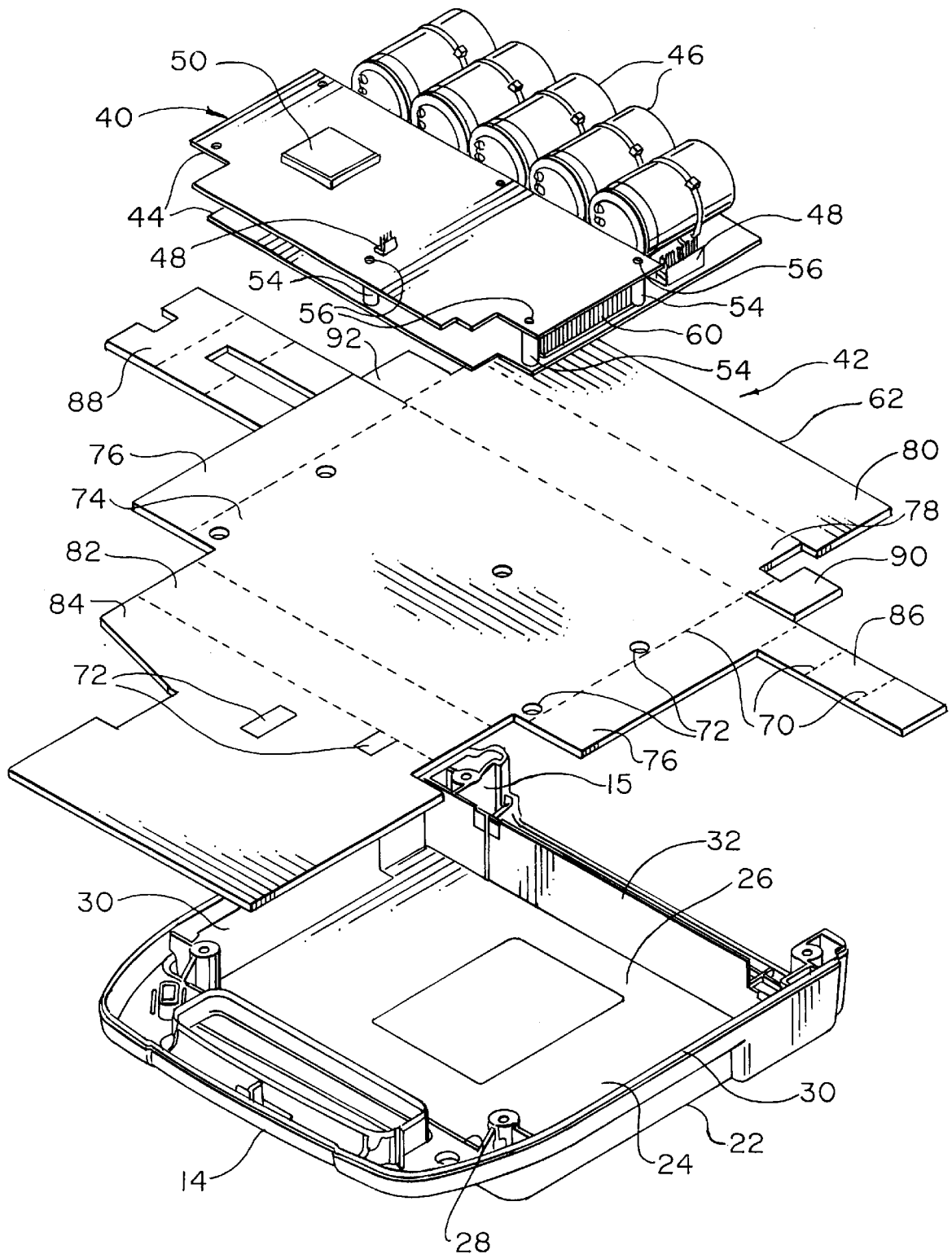
FIG. 2 is an exploded perspective view of a portion of an AED.
Figure 3:
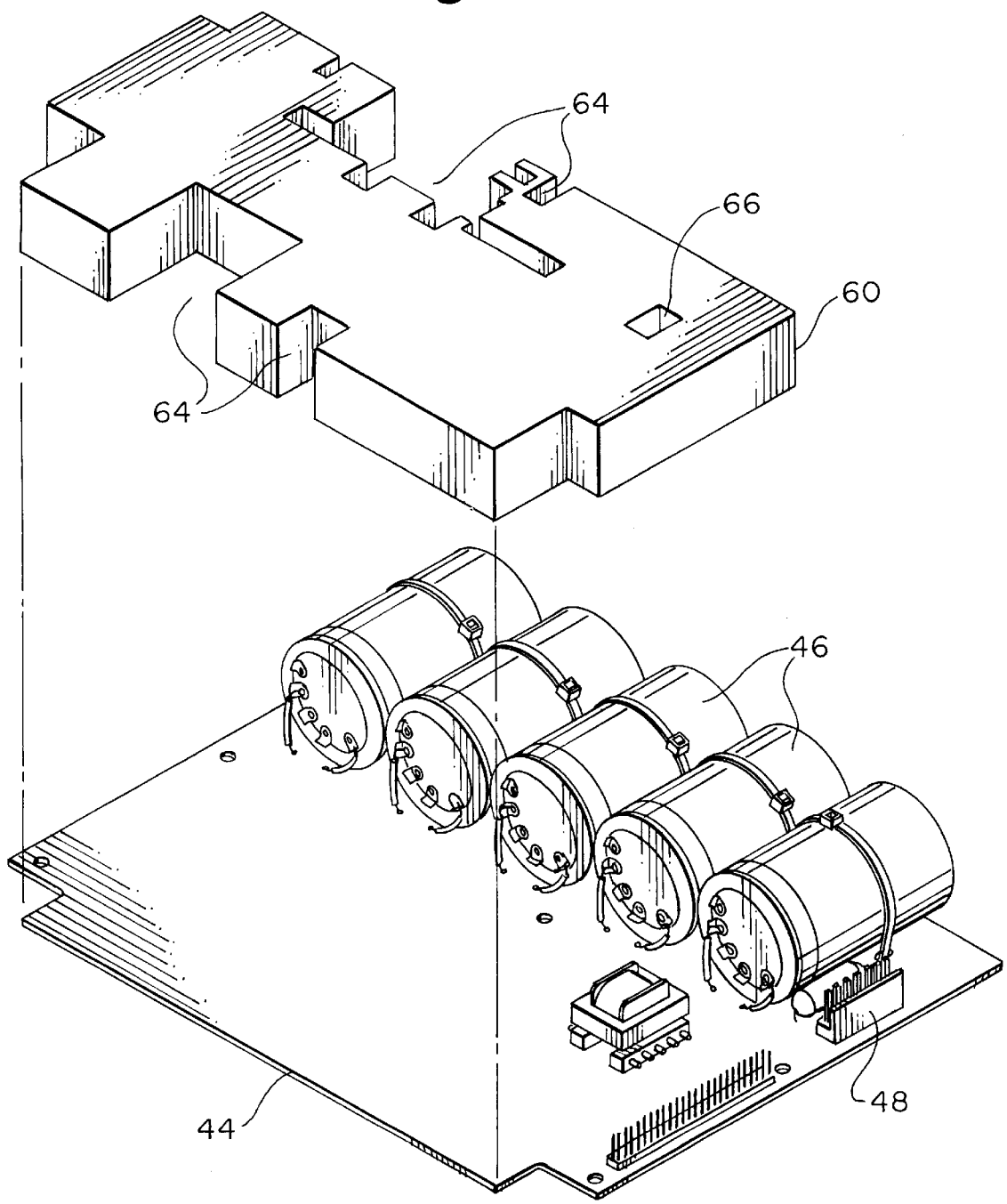
FIG. 3 is an exploded perspective view showing a spacer positioned above a circuit board.

Now referring to FIGS. 1–2, AED 10 includes a plastic case (or AED housing) 12 with a carrying handle 14 and a battery compartment 15. Case 12 also includes an electrode compartment (not shown) which is enclosed by lid 18. Structurally, case 12 is formed by mating and securing upper portion 20 and lower portion 22.

Within the electrode compartment, a pair of defibrillator electrodes (not shown) can be stored for use with AED 10. Suitable packaged electrodes for use with AED 10 are disclosed in the Gilman et al. U.S. Pat. No. 5,402,884, the disclosure of which is hereby incorporated by reference. These electrodes are also commercially available from SurVivaLink Corporation.

Figure 7:
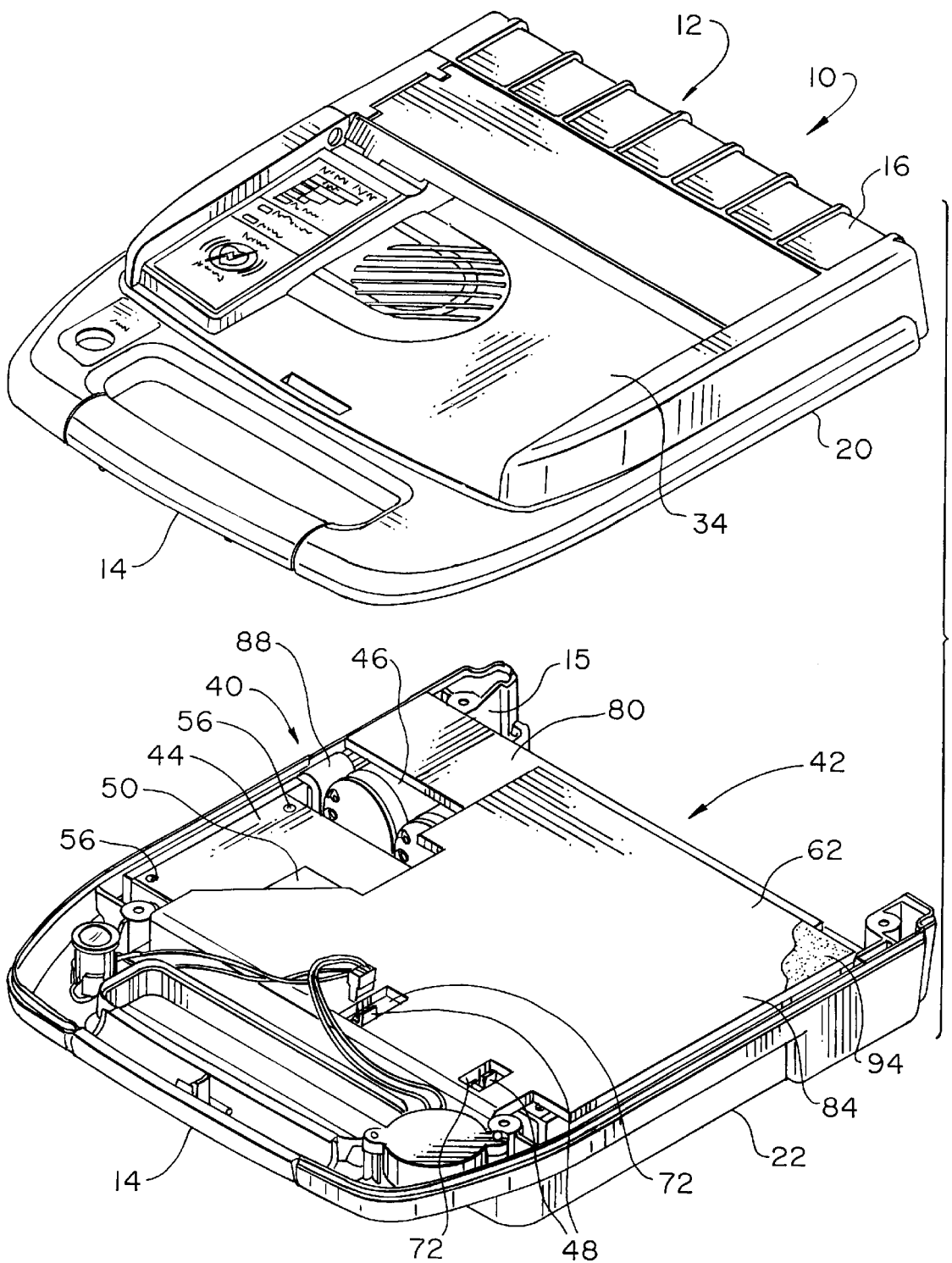
FIG. 7 is a perspective view of the electronic circuitry system of FIG. 6 in place and with front and rear fold over panels folded thereover.

Referring now to FIGS. 2 and 7, a chamber 24 is formed within lower portion 22. When case 12 is assembled, chamber 24 is bounded by a bottom 26 of case lower portion 22, a front side 28, two lateral sides 30, a rear side 32, and bottom 34 of case upper portion 20. When AED 10 is fully assembled and ready for use, chamber 24 accommodates the circuit boards and other electronic components of AED 10 as more fully described below.

Figure 4:
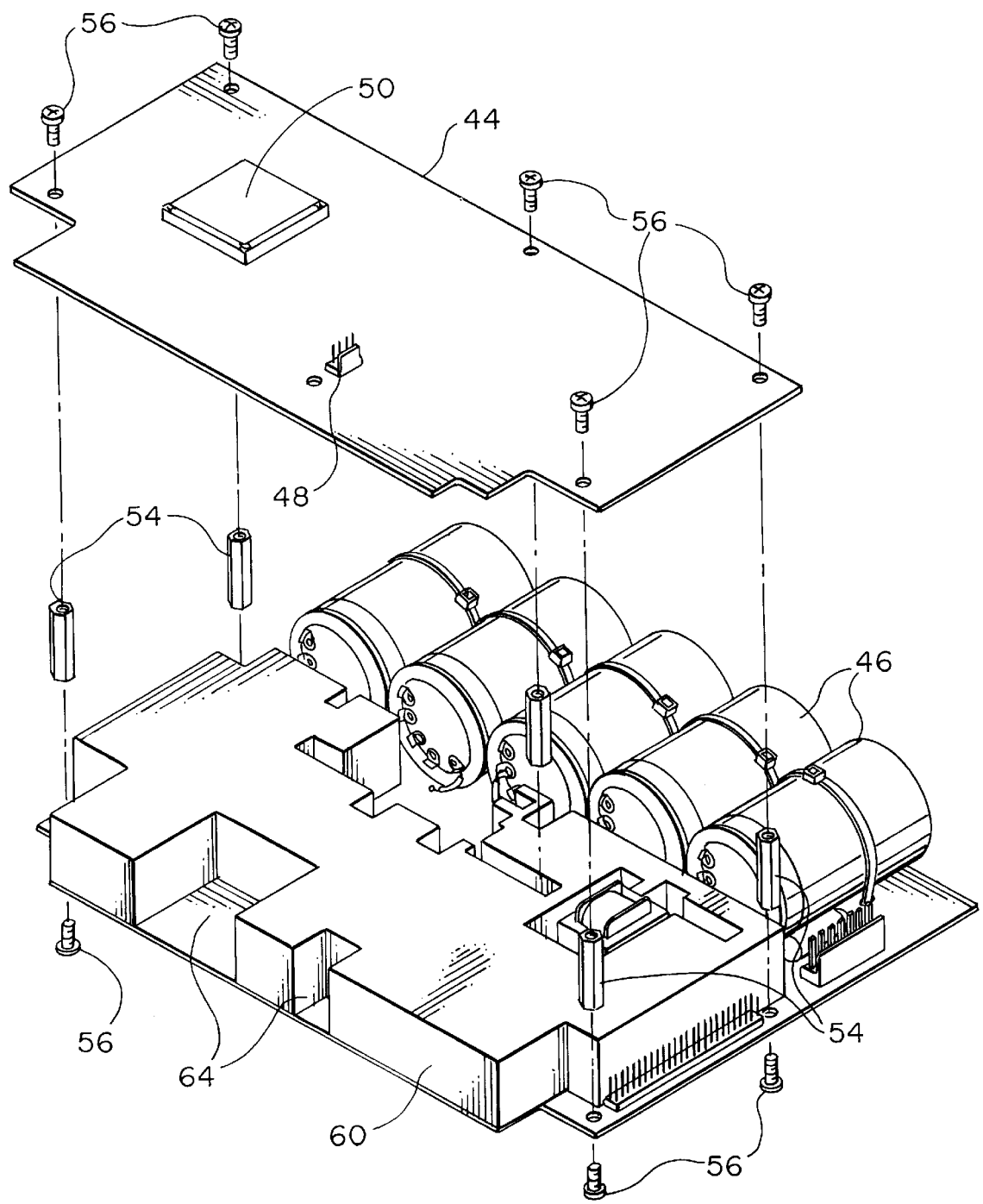
FIG. 4 an exploded perspective view showing a second circuit board positioned above the spacer and first circuit board.
Figure 5:
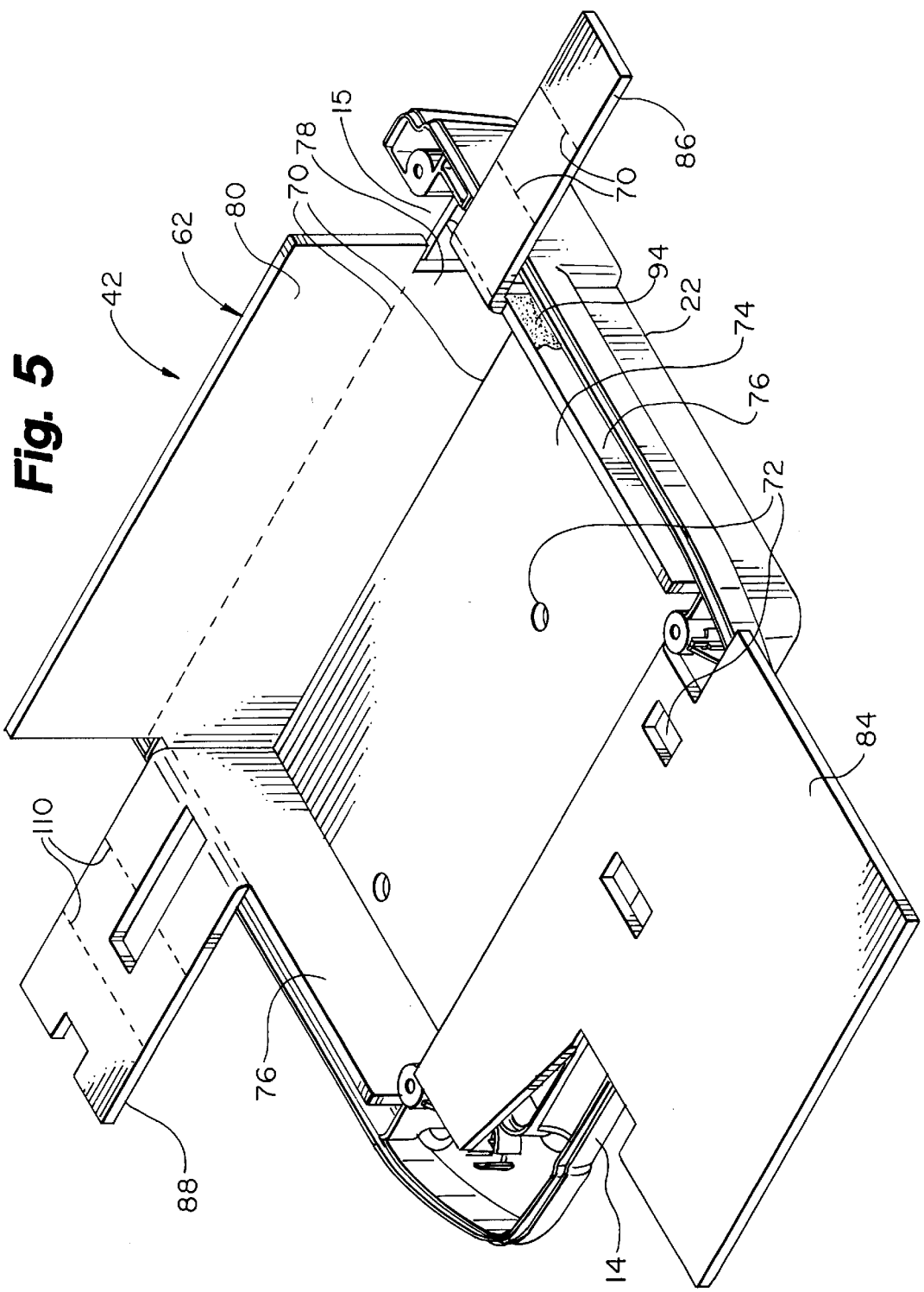
FIG. 5 is a top perspective view showing a shock mount positioned in a lower portion of an AED case.
Figure 6:
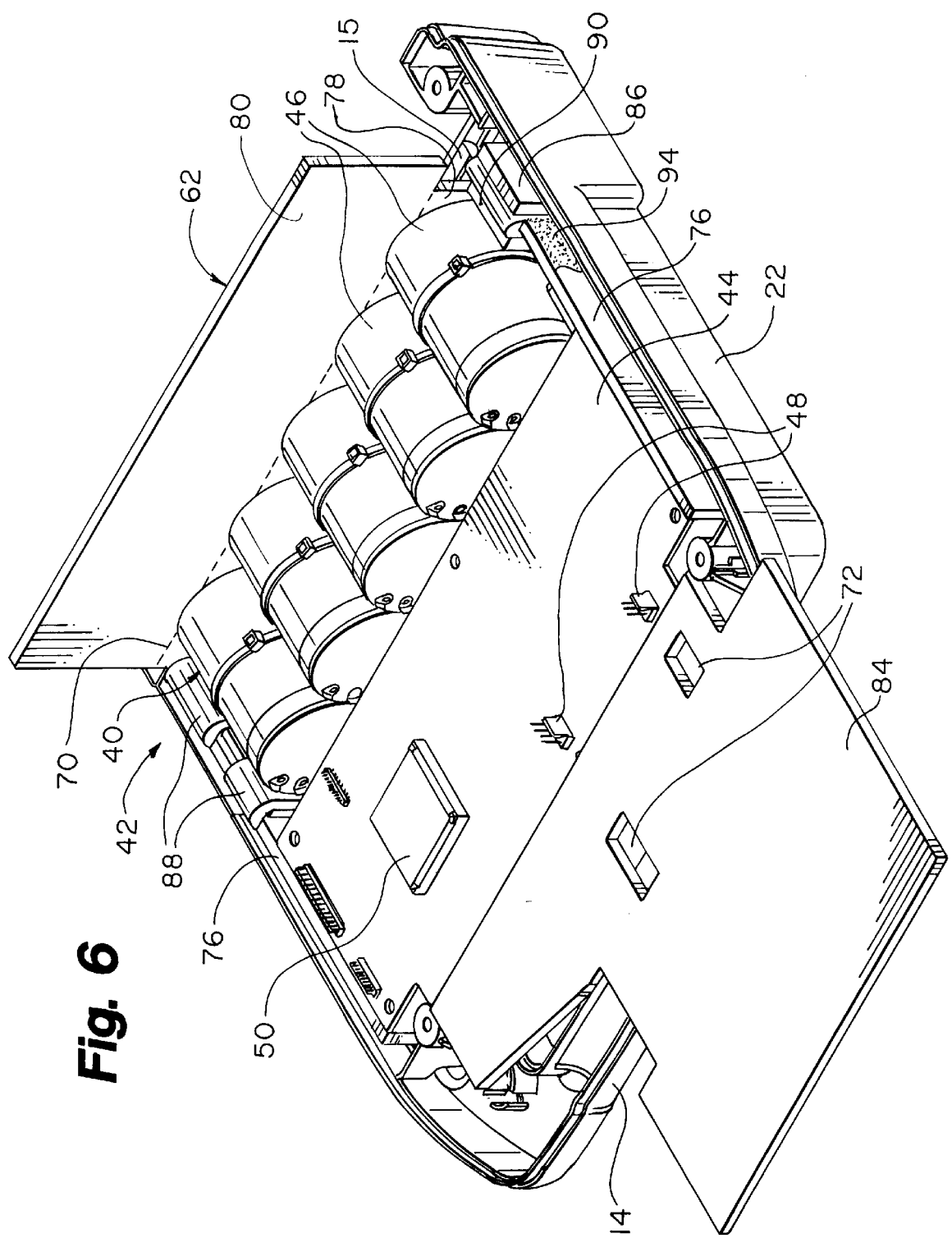
FIG. 6 is a perspective view with a spacer disposed between two circuit boards and in place within the shock mount of FIG. 5.

As seen in FIGS. 2, 4, and 7, when AED 10 is fully assembled, various components of an electronic circuitry system 40 and circuit mounting system 42 are disposed within chamber 24. Electronic circuitry system 40, includes one or more circuit boards 44. Present on the surface of any of circuit boards 44 may be such electronic components as capacitors 46, terminals 48, and semiconductor chips 50. When present, these elements are raised above the surface of a circuit board 44. A pair of circuit boards 44 may be fastened together by means of a number of standoffs 54 and fastening devices such as screws 56.

FIGS. 2–7 depict circuit mounting system 42, which includes a mounting structure or spacer 60 and another mounting structure or shock mount 62. Spacer 60 is preferably a die cut piece of mounting foam and includes any number of cut out portions 64 to accommodate the dimensions and components of a circuit board 44. Spacer 60 may also include any number of depressions 66 also to accommodate various components of electronic circuitry system 40. Spacer 60 is preferably made of a closed cell, low density polyethylene, and more preferably made of a polyurethane polyester foam with a density of two pounds per cubic foot, a tensile strength of 15 psi, and a tear strength of 1.5 psi. A suitable polyester foam for spacer 60 may be obtained from Flextech, Inc., of New Hope, Minn. In this embodiment, spacer 60 is about 4.3" wide, about 9.0" long, and about 1.0" thick. It should be noted that greater or lesser dimensions may be used without departing from the spirit or scope of the present invention. The actual dimensions of spacer 60 are determined by the dimensions of the circuitry and case of the AED in which spacer 60 is installed.

As best seen in FIG. 2, shock mount 62 includes a series of scorings (or perforations) 70 and may include a plurality of die cut openings 72. Scorings 70 define a number of panels and tabs within shock mount 62. Panels defined by scorings 70 include bottom panel 74, two side panels 76, rear panel 78, rear fold over panel 80, front panel 82, and front fold over panel 84. Lateral segmented tabs 86, 88 extend from side panels 76, while lateral segmented tabs 90, 92 extend from rear panel 78. Ideally, shock mount 62 is made of a microcellular urethane foam with a density of fifteen pounds per cubic foot, a tensile strength of 40 psi, and a tear strength greater than 7 psi. In this embodiment, the urethane foam from which shock mount 62 is made is about 0.2" in thickness. However, other thicknesses would be preferable if other foams were used. If the urethane with the previously described properties is used, it may be obtained from Flextech, Inc., of New Hope, Minn. Optionally, a metal foil or other shielding 94 may be affixed to an exterior surface of shock mount 62 such that components of electronic circuitry system 40 are protected from electromagnetic interference. In one embodiment, metal foil shielding 94 is aluminum foil bonded to shock mount 62 by a pressure sensitive adhesive. Ideally, these metal foils are 0.002" to 0.005" in thickness. However, greater or lesser thicknesses may be used. Alternatively, netting made of conductive materials may be employed. Commercial quantities of these shielding materials may be obtained from several sources readily known by those skilled in the art.

Spacer 60 and shock mount 62 are used in the assembly of the electronic circuitry components of AED 10. During assembly, spacer 60 is disposed between two circuit boards 44. Standoffs 54 are then placed into position and screws 56 used to secure circuit boards 44 in a fixed position with spacer 60 therebetween.

Shock mount 62 is then placed within chamber 24 by folding side panels 76, rear panel 78 and front panel 82 upwardly from bottom panel 74. Assembled circuit boards 44 and spacer 60 are then placed atop bottom panel 74 within chamber 24. Lateral segmented tabs 86–90 are then folded, ideally doubled, to accommodate wiring (not shown) which is connected to terminals 48 on the assembled electronic circuitry system 40. These wires include leads extending to electrodes and batteries. By folding and doubling, segmented tabs 86–92 these leads are therein further insulated and are protected from sharp corners and from abrading against assembled components of electronic circuitry system 40 during use. Rear fold over panel 80 is then folded inwardly over such circuitry components as capacitors 46. Finally, front fold over panel 84 is folded inwardly over an otherwise exposed circuit board 44. Electronic circuitry system 40 is now ready to be connected to other operative components of AED 10 and is installed within circuit mounting system 42. After these connections are made, case upper portion 20 is then mated to case lower portion 22 and affixed thereto by such means as screws or rivets.

In FIGS. 8–11, circuit mounting system 102 illustrates another embodiment of the present invention. Circuit mounting system 102 includes at least one mounting structure 104. Each mounting structure 104 includes a series of scorings (or perforations) 70, thereby defining a bottom panel 106, two side panels 108, a rear panel 110, and a front panel 112. In this embodiment, bottom panel 106, side panels 108, rear panel 110 and front panel 112 may have the same dimensions as their counterparts formed in shock mount 62. Disposed within the panels of mounting structure 104, and preferably within bottom panel 106, are a plurality of receiving cavities 114. Receiving cavities 114 are preferably die cut from the materials used to make mounting structure 104. However, depressions 115 may also be present. Mounting structure 104 is preferably a foam such as that used for spacer 60 or for shock mount 62.

Alternatively, a metal foil 116, as shown in FIG. 11, may be bonded to an exterior surface of mounting structure 104. Metal foil 116 protects circuit board 44 from electromagnetic interference and may be made of the same materials as metal foil 94. Circuit board 44 may have a number of components extending from the surface of the circuit board itself. Receiving cavities 114 on mounting structure 104 may be molded or otherwise formed to accommodate these structures. In assembly, mounting structure 104 is placed in chamber 24 and folded along scorings 70 such that panels 108–112 follow the contours of sides 28–32 of case lower portion 22. Circuit board 44 is then placed atop bottom panel 106 such that structures extending from the bottom surface of circuit board 44 (e.g. terminals 48, chips 50) are accommodated by receiving cavities 114 or depressions 115. Other components extending from a surface of circuit board 44 include terminals, screws, and stand offs. The maximum compression of the foam, of which mounting structure 104 is made, is controlled by the relative thickness of the foam itself as well as its density. A clearance of approximately one-quarter (¼ T) of the overall thickness (T) of the foam is ideally provided between chip 50 and the bottom of the foam mounting structure 104.

The invention is not to be taken as limited to all the details thereof as modification and variations thereof may be made without departing from the spirit or scope of the invention. The invention rather is to be interpreted by the scope of the claims appended herein.

What is claimed is:

1. An automated external defibrillator system, comprising:
   an automated external defibrillator housing;
   an electronic circuitry system disposed within the housing; and
   a foam mounting structure protectively disposed about the electronic circuitry system, the foam mounting structure further including an electromagnetic shielding material attached to an exterior surface thereof.

2. The automated external defibrillator system of claim 1, wherein the electronic circuitry system includes first and second circuit boards.

3. The automated external defibrillator system of claim 2, further comprising a foam spacer disposed between the first and second circuit board.

4. The automated external defibrillator system of claim 3, wherein the foam spacer is a low density die cut foam.

5. The automated external defibrillator structure of claim 1, wherein the shielding material is aluminum foil.

6. The automated external defibrillator system of claim 1, wherein the foam mounting structure further includes a plurality of scorings, thereby defining a series of panels, the panels accommodating horizontal and vertical dimensions of an interior portion of the automated external defibrillator housing.

7. The automated external defibrillator system of claim 1, wherein the foam mounting structure is a closed cell low density polyethylene.

\* \* \* \* \*